(12) United States Patent
Harvey

(10) Patent No.: US 7,630,859 B2
(45) Date of Patent: Dec. 8, 2009

(54) METHOD AND APPARATUS FOR REDUCING THE EFFECTS OF WINDOW CLOUDING ON A VIEWPORT WINDOW IN A REACTIVE ENVIRONMENT

(75) Inventor: Kenneth C. Harvey, Dallas, TX (US)

(73) Assignee: Verity Instruments, Inc., Carrollton, TX (US)

( * ) Notice: Subject to any disclaimer, the term of this patent is extended or adjusted under 35 U.S.C. 154(b) by 0 days.

(21) Appl. No.: 11/799,516

(22) Filed: May 1, 2007

(65) Prior Publication Data

US 2008/0275658 A1 Nov. 6, 2008

(51) Int. Cl.
*G06F 11/30* (2006.01)
*G06F 17/40* (2006.01)
(52) U.S. Cl. .................. 702/182; 702/30; 702/183; 702/187
(58) Field of Classification Search .............. 702/30, 702/182–189; 250/573; 356/343; 216/60
See application file for complete search history.

(56) References Cited

U.S. PATENT DOCUMENTS

| | | | |
|---|---|---|---|
| 5,347,138 A * | 9/1994 | Aqui et al. ............... 250/573 |
| 5,348,614 A | 9/1994 | Jerbic | |
| 5,352,902 A | 10/1994 | Aoki | |
| 5,536,359 A | 7/1996 | Kawada et al. | |
| 5,897,378 A | 4/1999 | Eriguchi | |
| 5,966,586 A | 10/1999 | Hao | |
| 5,985,032 A | 11/1999 | Eriguchi | |
| 6,129,807 A | 10/2000 | Grimbergen et al. | |
| 6,269,278 B1 | 7/2001 | Smith, Jr. et al. | |
| 6,278,809 B1 | 8/2001 | Johnson et al. | |
| 6,344,151 B1 * | 2/2002 | Chen et al. ............... 216/60 |
| 6,540,587 B1 | 4/2003 | Gotkis et al. | |
| 6,603,538 B1 | 8/2003 | Oluseyi et al. | |

(Continued)

OTHER PUBLICATIONS

Giuseppe Fazio, Pietro Petruzza, and Alessandro Spandre, New Optical Range Inspection and Improving Optical Response for Spectroscopic Base Endpoint Detection, Future Fab Intl. vol. 20, Jan. 7, 2006. (http://vvww.future-fab.com/documents.aso?d ID=3710) (last visted Apr. 30, 2007).

(Continued)

*Primary Examiner*—Eliseo Ramos Feliciano
*Assistant Examiner*—Phuong Huynh
(74) *Attorney, Agent, or Firm*—Rudolph J. Buchel, Jr.

(57) ABSTRACT

The present invention is directed to a method and apparatus for reducing the effects of window clouding on a viewport window in a reactive environment. One or more clouded viewport windows are obtained for testing, in which the clouding results from exposure to the reactive environment. The clouding typically appears as a coating film on the test windows. The clouded viewport windows are analyzed for one or more spectral regions having good transmission. The threshold level of light transmission is determined by the particular application in which the window is used. The spectral regions of good transmission are evaluated for their usefulness with a particular algorithm that will use the spectral data in a production environment. Spectral regions that cannot be evaluated using the subject algorithm are eliminated from consideration. Spectral regions that can be evaluated using the subject algorithm and exhibit low absorption are selected for monitoring in the production environment.

31 Claims, 8 Drawing Sheets

U.S. PATENT DOCUMENTS

| | | | |
|---|---|---|---|
| 6,740,196 B2 | 5/2004 | Lee et al. | |
| 6,750,977 B2 | 6/2004 | Otsubo et al. | |
| 6,835,275 B1 | 12/2004 | Grimbergen et al. | |
| 6,919,279 B1 | 7/2005 | Rulkens et al. | |
| 7,074,310 B2 * | 7/2006 | Smalley et al. | 204/450 |
| 7,102,132 B2 | 9/2006 | Ludviksson | |
| 7,172,969 B2 | 2/2007 | Xia et al. | |
| 2003/0016354 A1 * | 1/2003 | Hui | 356/328 |
| 2005/0060103 A1 * | 3/2005 | Chamness | 702/30 |
| 2005/0173375 A1 * | 8/2005 | Mitrovic et al. | 216/60 |

OTHER PUBLICATIONS

Oriel Integrating Spheres, Specification Sheet, Newport Corporation (newport.com/file_store/PDFs/.../e5496_Oriel-Integrating-Spheres.pdf) (last visited Apr. 30, 2007).

* cited by examiner

Measured Transmission of Clouded Windows. Window 1: Lightly Clouded, Window 2: Marginally Clouded, Window 3: Highly Clouded.

Measured Transmission of Highly Clouded Window

Typical Endpoint Trend

Trends for 47 Data Files During a
Fourteen Day Period

METHOD AND APPARATUS FOR REDUCING THE EFFECTS OF WINDOW CLOUDING ON A VIEWPORT WINDOW IN A REACTIVE ENVIRONMENT

CROSS REFERENCES TO RELATED APPLICATIONS

The present application is related to the following co-pending U.S. patent application: U.S. patent application entitled, "Multichannel Array as Window Protection", having application Ser. No. 11/726,958, and filed on Mar. 21, 2007, currently pending, which is assigned to the assignee of the present invention. The above identified application is incorporated by reference herein in its entirety.

BACKGROUND OF THE INVENTION

The present invention relates generally to obtaining accurate optical emission spectroscopy measurements in a plasma environment in which optical sensor window films are present. More particularly, the present invention relates to a system and method to utilize the near infrared region of the electromagnetic spectrum to obtain measurements through a clouded window, with a low absorption of light, which avoids the large light absorption in the ultraviolet and visible light.

DESCRIPTION OF RELATED ART

In the art of semiconductor processing, in order to form integrated circuit structures from wafers, selectively removing or depositing materials on a semiconductor wafer is well known. Removal of material from a semiconductor wafer is accomplished by employing some type of etching process, for instance and including reactive ion etching, deep-ion etching, sputtering etching and plasma etching. Depositing material on a wafer may involve chemical and physical vapor depositions, evaporative deposition, electron beam physical vapor deposition, sputtering deposition, pulsed laser deposition, molecular beam epitaxy and high velocity oxygen deposition. Other removal and deposition processes are known. Such processes are tightly controlled and are done in a sealed process chamber. Because exact amounts of material are deposited onto or removed from the substrate wafer, its progress must be continually and accurately monitored to precisely determine the stopping time or endpoint of a particular process. Optically monitoring the chamber processes is one very useful tool for determining the stage or endpoint for an ongoing process. For instance, the interior of the chamber may be optically monitored for certain known emission lines by spectrally analyzing predetermined wavelengths of light emitted or reflected from the target in the chamber. Typical methods are optical emission spectroscopy (OES), absorption spectroscopy, reflectometry, etc. Typically, an optical sensor or source is positioned on the exterior of the chamber and adjacent to a viewport or window, with a vantage point to the target area in the chamber to be observed.

One problem with optical monitoring chamber processes is that during many of these processes, the interior of the chamber contains alloys, polymers and reactive gases that result in deposits on the interior surfaces of the chamber, including the viewport window. Additionally, the window is subject to etching, and further degradation, by the reactive gases in the chamber. As the window becomes clouded, its optical properties are altered, which may affect the measurements by the optical sensor. While it is expected that the entire interior surface of the chamber must be cleaned of deposits from time to time, and the chamber recertified, the window must be cleaned or replaced much more frequently for maintaining consistently accurate optical measurements. Under certain conditions, the viewport window must be cleaned ten or twenty times, and the optical sensor recalibrated, between chamber cleanings. Maintaining the chamber window is time consuming, expensive and decreases the available runtime of the chamber.

Typically, the prior art handles window clouding in one of three ways to reduce the frequency between window maintenance between chamber cleaning cycles: adjusting the optical measurements to account for window clouding; in situ cleaning of the window; and preventing the optical degradation of the window. There is no single method for adjusting the optical measurements to suit all situations and processes. The success of these methods varies on a case by case basis, by the particular process, and even by the spectral wavelength being monitored for a process. In situ cleaning typically involves some mechanism for cleaning the viewport window without removing the window and with little interruption to the process schedule. One method is to direct an inert gas toward the exterior surface of the window to remove contaminants from the window. Gases such as helium and nitrogen are often used, but other, non-inert gases, may also aid in cleaning the viewport window, such as $O_2$. However, the use of an inert gas on a window (or any non-process gas) that is exposed to the interior of the chamber and mixes with the process gas may adversely affect the process. U.S. Pat. No. 6,052,176 to Ni, et al., entitled "Processing Chamber With Optical Window Cleaned Using Process Gas" discloses using a process gas to remove contaminants from the window. A port for the process gas is oriented parallel to the exterior window surface. The process gas flow dislodges any by-products from the surface of the window and then directs the same onto the processing chamber. U.S. Pat. No. 6,344,151 to Chen, et al., entitled "Gas Purge Protection of Sensors and Windows in a Gas Phase Processing Reactor," discloses a gas purged viewport for endpoint detection in a gas phase processing chamber which prevents contamination of an optical monitoring window by use of a purge gas flow. The gas purge viewport includes a prechamber between the optically transparent window and the process chamber. The purge gas is passed through the prechamber and into the processing chamber to purge the window. Chen, et al. discuss using the gas purge system to purge other parts of the system, including sensors exposed to the chamber. U.S. Pat. Nos. 6,390,019 and 6,712,927 to Grimbergen, et al., entitled "Chamber Having Improved Process Monitoring Window," disclose using energized process gas ions to energetically bombard the window and remove process residues deposited thereon. An electric field source comprises an electrode with one or more apertures which is disposed between a window and light source to provide an electric field that is perpendicular to the plane of the window and accelerate process gas ions toward the window.

The use of purge gas, even process gases, may reduce the flow of process gas to the shower and result in a detrimental effect on the process. U.S. Pat. No. 6,301,434 to McDiarmid, et al., entitled "Apparatus and Method for CVD and Thermal Processing of Semiconductor Substrates," discloses a dual gas injection manifold which is used in a thermal processing system, which has a purge gas showerhead on its top surface and a process gas showerhead on its bottom surface. The manifold prevents unwanted deposition on the underside of the window, as well as injects the reactant gas for deposition and etching.

Preventing window clouding before it influences the optical properties of the window would seem to be the most viable solution to clouding, yet, heretofore has not yielded complete success. Preventing contaminants from reaching the viewport window often involves restricting the size of the passage(s) to the window. U.S. Pat. No. 6,762,849 to Rulkens entitled "Method for In-Situ Film Thickness Measurement and Its Use for In-Situ Control of Deposited Film Thickness," discloses installing a fine metal mesh screen or bundle of small diameter tubes over the internal surface of the optical port entry for protecting the window. U.S. Pat. No. 4,407,709 to Enjouji, et al. entitled "Method and Apparatus for Forming Oxide Coating by Reactive Sputtering Technique," discloses a window with slits for preventing clouding of the viewport window of a sputtering apparatus.

Another technique is to place a restrictor plate between the window and chamber that inhibits the passage of contaminants to the window. U.S. Pat. No. 6,170,431 to DeOrnellas, et al., entitled "Plasma Reactor with a Deposition Shield" discloses a reactor that includes a shield that prevents the deposition of materials along a line-of-sight path from a wafer toward and onto a window. The shield is comprised of a plurality of louvers or slats which are positioned at a skewed angle with respect to the wafer. However, this particular configuration would also inhibit line-of-sight optical measurements. Other restrictor devices include protruding shield designs, such as taught by Nakata, et al., in U.S. Pat. No. 6,576,559 to Nakata, et al., "Semiconductor Manufacturing Methods, Plasma Processing Methods and Plasma Processing Apparatuses." There, the protruding shield has an angular cylindrical shape and is disposed between a laser source and window to prevent reaction generated material from intruding into the inner surface of the window as much as possible. The magnitude of gaps between shields is determined by properties of the laser beam and the scanning operation to be carried out by the laser galvano mirror. Brcka discloses, in U.S. Pat. No. 6,666,982 entitled "Protection of Dielectric Window in Inductively Coupled Plasma Generation," protecting a dielectric window in an inductively coupled plasma reactor from depositions of coating or etched material with a slotted shield, however the slots permit some material to pass toward the window.

Other prior art window clouding restrictors include the notion of the mean free path of the molecules to be restricted. U.S. Pat. No. 5,145,493 to Nguyen, et al., entitled "Molecular Restricter," discloses a restricter plate with cell dimensions based on mean free path of the molecules to be restricted. The molecular restricter comprises a plate with at least one elongated cell with parallel walls and open ends, wherein the cell has a width and length. Optimally, Nguyen, et al. report that the width should be less than one mean free path and the length of the cells should be greater that ten times the mean free path. Nguyen, et al. further assert that for an aspect ratio of 2/1 (length/width), the molecular transmission is about half of that where it is 1/1. At a ratio of 5/1, only about 9% is transmitted, on down to about 1% transmitted at a ratio of only about 12.5/1. Aqui, et al. also disclose, in U.S. Pat. No. 5,347,138 entitled "In Situ Real Time Particle Monitor for a Sputter Coater Chamber," the use of mean free path to determine the dimensions of shield tubes open to a chamber, but for use on metal atoms dislodged from a target by a laser beam. Aqui, et al. state that the optimal width of the shield tubes is equivalent to less than one mean free path and their length are three times the mean free path or greater.

Still other attempts at preventing window clouding employ both a restrictor and the use of purge gas. U.S. Pat. No. 5,681,394 to Suzuki entitled "Photo-Excited Processing Apparatus and Method for Manufacturing a Semiconductor Device by Using the Same," discloses a photo-excited processing apparatus that includes a reaction chamber filled with reaction gas, photo-excitation irradiating light source and a light transmissive window between the light source and chamber. A multi-holed transparent diffusion plate is arranged between the light transmissive window and a substrate in the chamber. However, the thickness of this diffusion plate is not discussed. Purge gas, either $N_2$ or $O_2$, enters between the transmissive window and the transparent diffusion plate. The combination of the diffusion plate and purge gas suppresses depositions to the surface of the light transmissive window. U.S. Pat. No. 6,110,291 to Haruta, et al. entitled "Thin Film Forming Apparatus Using Laser," discloses introducing a clean purge gas, such as oxygen, through a pipe directly at the window (either the laser window or a sensor window) in order to clean the window. Additionally, Haruta, et al. teach the placement of an aperture and, alternatively, an elongated grid between the chamber and window so that the solid angle between the laser window and target is smaller in order to reduce the amount of dust that accumulates on the window.

BRIEF SUMMARY OF THE INVENTION

The present invention is directed to a method and apparatus for reducing the effects of window clouding on a viewport window in a reactive environment. One or more clouded viewport windows are obtained for testing, in which the clouding results from exposure to the reactive environment. The clouding typically appears as a coating film on the test windows. The clouded viewport windows are analyzed for one or more spectral regions having good transmission. The threshold level of light transmission is determined by the particular application in which the window is used. The spectral regions of good transmission are evaluated for their usefulness with a particular algorithm that will use the spectral data in a production environment. Spectral regions that cannot be evaluated using the subject algorithm are eliminated from consideration. Spectral regions that can be evaluated using the subject algorithm and exhibit low absorption are selected for monitoring in the production environment.

BRIEF DESCRIPTION OF THE SEVERAL VIEWS OF THE DRAWINGS

The novel features believed characteristic of the present invention are set forth in the appended claims. The invention itself, however, as well as a preferred mode of use, further objectives and advantages thereof, will be best understood by reference to the following detailed description of an illustrative embodiment when read in conjunction with the accompanying drawings wherein:

Figure 1:
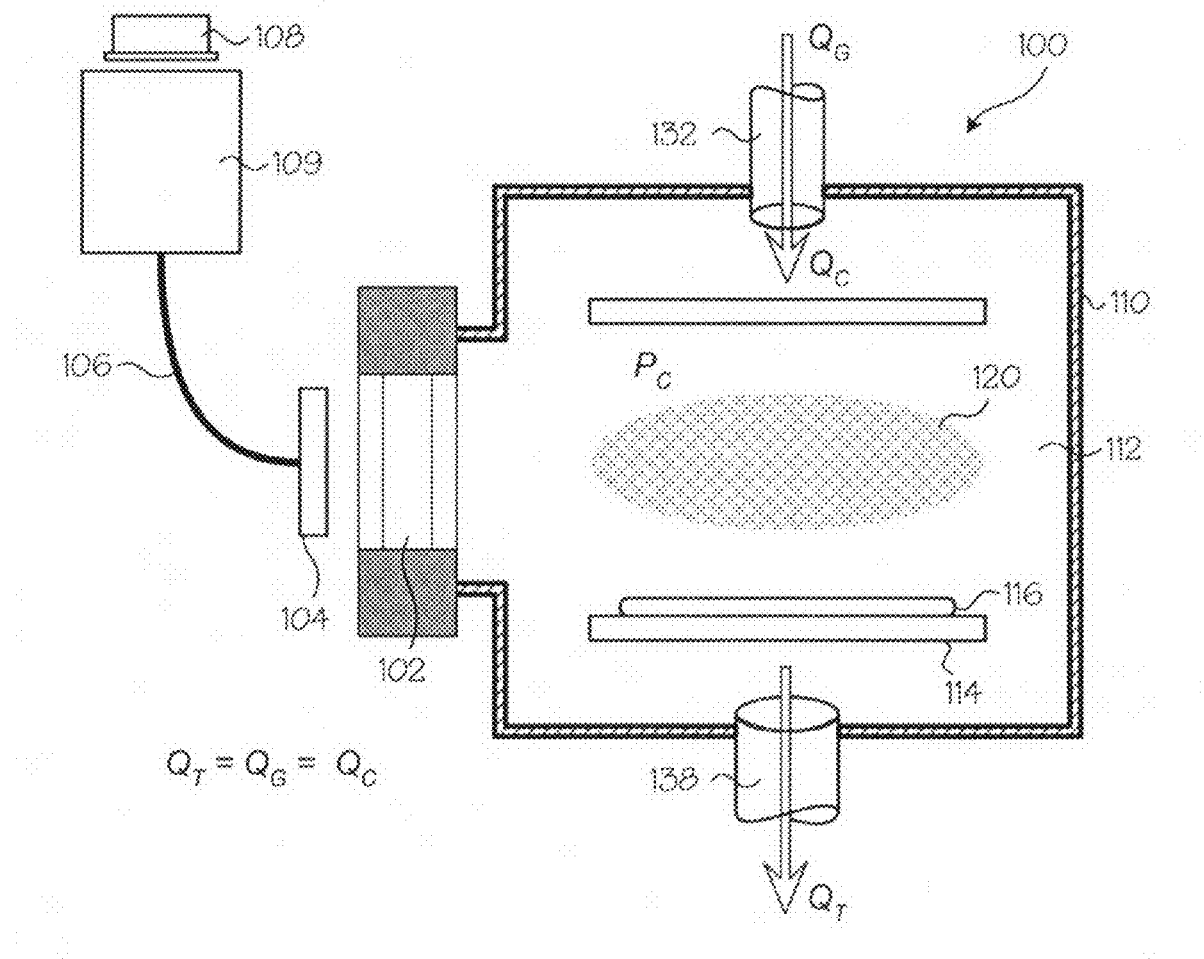
FIG. 1 is a diagram of a system for obtaining accurate OES measurements in accordance with an exemplary embodiment of the present invention.

Other features of the present invention will be apparent from the accompanying drawings and from the following detailed description.

DETAILED DESCRIPTION OF THE INVENTION

Element Reference Number Designations

| |
|---|
| 100: OES Measurement Apparatus |
| 102: Window |
| 104: Collecting Optics |
| 106: Optical Fiber |
| 108: Sensor |
| 109: Spectrograph |
| 110: Processing Chamber |
| 112: Interior Of Processing Chamber |
| 114: Wafer Support |
| 116: Wafer |
| 120: Plasma |
| 132: Process Gas Inlet (Shower Head) |
| 138: Processing Chamber Gas Outlet |
| 200: Test Measurement Apparatus |
| 202: Window |
| 203: Source Lamp |
| 205: Integrating Sphere |
| 208: Sensor |
| 209: Spectrograph |

A high-quality optical path is a necessity to perform most spectroscopic techniques, such as optical emission spectroscopy (OES) and reflectometry. Any obstruction that affects the intensity of the radiation degrades the accuracy and reliability of the technique. The obstruction may alter the intensity as a function of the wavelength. Typically, an optical sensor is positioned outside a process chamber and adjacent to a viewport window for obtaining optical measurements of a target within a process environment, (the process environment may be a process chamber, or along the up- or downstream piping associated with a processing chamber). Understanding the optical properties of these windows is critical for obtaining accurate measurements through them. As a viewport window becomes clouded, its optical properties change, sometimes in detrimental ways. Deposits must be cleaned from the viewport window, or the window replaced, in order to maintain a high-quality optical path.

The problems associated with window clouding continues to plague the semiconductor industry. The origin of particles may be from reaction products on the chamber wall that flake off. Alternatively, these particles may be formed from the plasma chemistry and might coalesce in the plasma, or be a byproduct of some other high energy reaction, such as from a laser.

The particles in the chamber may diffuse to the window surface. The equation for Brownian motion is described below.

$$\overline{x^2} = \frac{kT}{3\pi \cdot \eta \cdot a} \cdot t \quad (1)$$

where $\overline{x^2}$ is the mean square displacement of the particles,
a is the radius of particle,
t is the time,
T is the temperature of the media, and
ρ is the viscosity.

Particulates may migrate to the window by thermo-mechanical effects or turbulence, e.g., movement from turbulence when the chamber is back-filled, etc. Therefore, care should be taken when back-filling a chamber. Additionally, particulates may move toward the window as a result of thermal gradients, that is, they travel to the window by thermomolecular flow (or thermal transpiration) caused by a difference in temperature between the wafer and the window or thermal turbulence from the high temperature of the plasma, etc. Once at the window, the particulates may adhere to the window as a coating, resulting from either electrostatic attraction or chemisorption.

Reactive gases from the plasma and reaction products from the wafer may be transported to the window surface by diffusion, turbulence, thermal gradients, etc. At the window surface, these gases may change the optical transmission of the window in a number of ways. If reactive gases reach the window surface, they may bond to the surface by chemisorption, electrostatic attraction, etc. and form a film. If some material is being deposited, then the exact composition of the deposited material should be determined. Alternatively, or additionally, the window surface may be etched by the reactive gases. If the window is fused silica or glass, substituting sapphire as a window material may be advantageous as sapphire is more resistant to etching. Still further, it is possible that a change in the bulk composition of the window is caused by material dissolving into the window. For example, an alkali (Na, Cs, etc.) may dissolve in the quartz to produce a brown color. Radiation from the plasma may cause the optical properties of the window to change. Therefore, some of the gas components may photolyze in the window area and coat the window. Also, some of the constituent gases may chemisorb to the window and be transformed by photocatalysis to a material that coats the window.

Prior art techniques for solving the window clouding problem involve either adjusting the intensity of the light transmitted through the window to compensate for window clouding (for an optical window), altering the optical measurement algorithms to compensate for clouding (for a view port window) or techniques for decreasing the frequency of window maintenance (cleaning or replacing the window and recalibrating the optical sensors at the viewport). Techniques for adjusting the intensity of the light transmitted through the window based on the amount of window clouding are very difficult to implement as they vary with the specific implementation. In many cases, the best that can be achieved is merely to monitor the amount of chemical deposition that accumulates on the inner side of the viewport window within the reactor environment, see for instance U.S. Pat. No. 5,536,359 entitled "Semiconductor Device Manufacturing Apparatus and Method with Optical Monitoring of State of Processing Chamber," and then change the window when the accumulation on the window reaches a predetermined threshold amount of clouding.

Heating the window may reduce or eliminate coating to the window. This may reduce the sticking coefficient so that material does not stick initially to the window. Alternatively, it may help to evaporate or decompose material that is already deposited. It may be necessary to heat the window to as much as 200° C. to prevent the window from clouding. For a continuous mechanism, this may be done by adding heating elements to the window. Other methods might be heat lamps or high power lasers. For a pulsed mechanism, ablation of the absorbed material can be done with flash lamps or pulsed lasers.

Other prior art techniques designed to reduce the frequency of window cleaning include disposing a restrictor plate between the window and the chamber in order to reduce the amount of contaminants that reach the window and, alternatively, to clean the exterior surface of the window with a flow of purge gas. Restrictor plates are not completely effective and merely lessen the amount of contaminants that reach the window. The cross-sectional area of the restrictor apertures may be decreased to further reduce the amount of contaminants that make their way to the window, but smaller apertures tend to clog with contaminates more often than larger apertures. However, unlike cleaning or replacing a viewport window, a restrictor plate can be replaced with an identical plate without having to recalibrate the optical sensors to the new plate. Of course, whenever the window does become clouded, the optical sensors should be recalibrated to the replacement window.

Cleaning the window with purge gas presumes that contaminates have, or will reach the window, but these contaminates can be detached with a current of gas. Firstly, this assumption may be incorrect; the contaminants that reach the window may bind to the surface of the window. In any case, directing a purge gas to the window suffers from shortcomings that makes this technique impractical for certain applications. For instance, utilizing the process gas for the purge stream eliminates incompatibility problems that may be associated with using non-process gases. However, often the process gas itself reacts with the window material which causes clouding. Ultimately, it may be necessary to change the window material in order to use the process gas as the purge gas. Using a non-process gas for the purge gas enables the operator to select the optimal window material for the optical measurement to be taken without concern for the window reacting with the purge gas. Another benefit in using a non-process gas as the purge gas is that the purge gas may be selected for its cleaning properties for the particular type of contaminant. The drawback with using non-process gases as the purge gas is twofold. First, the purge gas will not entirely prevent the process gas from reaching and reacting with the window, so in selecting the type of window material, the susceptibility of clouding by the process gas should be considered. More importantly, the non-process gas will often have a detrimental affect on the process. Therefore, the purge flow rate of the non-process gas should be kept to an absolute minimum, which may worsen the clouding rate.

Furthermore, each of these purge gas techniques require a significant amount of redesign to the area surrounding the window viewport. For instance, the purge gas should have a sufficient flow rate and oriented in a suitable direction to wipe the exterior of the window of any contaminates that adhere to the window. This requires the port (or ports) either be aimed at the window to force a stream of gas directly on the surface of the window or to design a cavity adjacent to the window that facilitates gas flow in lifting contaminates off the surface of the window and propelling them back into the process chamber.

A multichannel array (MCA) is a plate that has channels in it. They have been put to many uses such as electron multipliers, atomic beam collimators, neutron collimators, windows, etc. These can be made of stainless steel, aluminum, exotic metals, etc. Typically, they are large with the diameter of the channel is d>0.1 mm. An MCA that is made of glass can have various sizes and some have channel diameters as small as 10 microns. Since glass is transparent at some wavelengths, it may be necessary to coat the outer surface of the multichannel array to maintain uniform transmission through the MCA as the outer surface becomes cloudy (coated).

A multichannel array is a way to prevent clouding. The multichannel array will act as a barrier to slow the transport to the window and a getter that collects material in the channels. Ultimately, material will begin to cloud the window. But this can be acceptable if the time between cleaning cycles is much less than the time that it takes to cloud the window.

1. The length L of channel should be greater than the mean free path $L_\alpha$ of the gas, or particulate, that will cloud the window, $L_\alpha << L$. This will slow the material that passes through the channel along the axis.
2. The diameter d of the channel should be less than the mean free path, $L_\alpha \geq d$. This will enhance sticking to the wall and reduce diffusion. However, the diameter of the channels should be large enough to avoid frequent blockage.
3. The channels should be cold so the material will stick to surfaces while it is moving through the channel.

None of the prior art techniques have had a substantial impact on the problem of window clouding. Many of these techniques are application-specific and require substantial modifications for each unique implementation. Most require substantial modifications be made to the system, usually at considerable expense, with only a marginal reduction in window clouding.

Recently, the inventor of the present application has disclosed a multichannel array structure for virtually eliminating clouding of an optical sensor viewport window in a plasma environment using a multichannel array with a back pressure between the multichannel array and viewport in a U.S. patent application entitled, "Multichannel Array as Window Protection", having application Ser. No. 11/726,958 and filed on Mar. 21, 2007, which is incorporated herein by reference in its entirety. By using the process gas to create the back pressure, this invention effectively eliminates window clouding without substantially altering the flow dynamics in the process chamber. However, in realizing these results, the window chamber is fitted with a multichannel array and is also ported for receiving process gases. What is needed is a method and system for obtaining usable optical emission spectroscopy (OES) measurements without modifying the window chamber.

Before describing the present invention, a further description into the background of the present invention may be helpful. Window clouding results from contaminants that adhere to the interior of a process chamber, such as chamber 110 shown in FIG. 1. These contaminants are essentially baked onto every surface of the interior volume 112 of process chamber 110, including the interior surface of optical viewport window 102. This residue creates a visible film that increases in thickness over time. If these contaminants are allowed to build up on surfaces in chamber interior 112, eventually they will flake off during operation and compromise the process performed therein. The effect of the contaminates on optical viewport window 102 is even more detrimental to a production process than residue in the chamber interior because the contaminate film on window 102 reduces the accuracy of the OES measurements long before the production process is affected by contaminate residue on chamber interior 112. Thus, viewport window 102 usually requires more frequent maintenance than chamber interior 112.

The type of clouding varies with the process performed in process chamber 110. For example, etch chemistries with $CF_x$ are widely used in the semiconductor industry. For optical measurements, these chemistries create a problem by coating windows with a substance with a polymer that is similar in many respects to PolyTetraFluoroEthylene (PTFE). That coating can, over time, absorb a large amount of light and reduce the amount of light that can be transmitted through the window. This large absorption of light affect the transmission of ultraviolet and visible radiation. Thus, optical emission spectroscopy (OES) and other measurements that utilize wavelengths in these regions will be detrimentally affected by this film coating on the window. Furthermore, since these wavelength regions are predominantly used in the semiconductor industry for process and diagnostic measurements, window clouding is a serious and ongoing problem with $CF_x$ etch chemistries.

Prior art efforts in overcoming window clouding problems have assumed that the large light absorption results from an opaque film deposited on the viewport window. This assumption may result from the film being opaque in the visible light spectrum (i.e., the film can be easily seen on a window), and is perhaps reinforced because the film is opaque to conventional measurement equipment employed in the semiconductor industry that uses Si-type CCD detectors. In fact, the vast majority of optical measurement equipment employed in the semiconductor industry is designed to operate in the ultraviolet through visible regions of the radiation spectrum. Thus, the problem of window clouding has assumed that the window film coating is opaque and, therefore, the overwhelming impetus of the semiconductor industry has been directed toward solving the problem of opaque window clouding, for environments that operate in ultraviolet-visible regions of the radiation spectrum.

Applicant, on the other hand, has discovered that the absorption of light in coating films due to, at least, $CF_x$ etch chemistries is not constant across the entire radiation spectrum. That is, certain window films that are nearly opaque in the ultraviolet (UV) through visible regions of the radiation spectrum, but exhibit extraordinarily good transmission at lower frequencies, such as in the near infrared (NIR) region of the radiation spectrum. In other words, Applicant understands that a more definitive solution to the window clouding problem is not to assume that the coating film is opaque, but instead to identify the spectral regions with low absorption and then to select sub-regions of the identified regions that are useful for performing a particular measurement. As mentioned above, since the prior art solutions to the window clouding problem have assumed that the coating film always increases the light absorption, these solutions have primarily involved adjusting the intensity of the light, altering the optical measurement algorithms to compensate for clouding or techniques for decreasing the frequency of window maintenance. Since the present invention does not presume that the window coating film is opaque, neither the light intensity or the optical measurement algorithms need be altered nor are any additional modifications to the window chamber necessary to decrease the frequency of window maintenance (although the benefits of present invention may be optimized when combined with certain modifications to the window chamber).

Before discussing the problem of light absorption further, a means for quantifying the amount of light transmission is needed, i.e., relative transmission, $l_T$. $l_T$ can be determined from the ratio of two measurements, the transmission with a window in the path of the radiation and a second transmission with the window out of the path of the radiation:

$$l_T = \frac{l_{in}}{l_{out}} \quad (2)$$

where $l_{in}$ is the transmission with the window in the path of the radiation, and $l_{out}$ is the transmission with the window out of the path of the radiation.

Relative transmission $l_T$ is scaled between 0.0 and 1.0, with 0.0 being completely opaque and 1.0 being completely transparent to the wavelengths of radiation being investigated.

Figure 2:
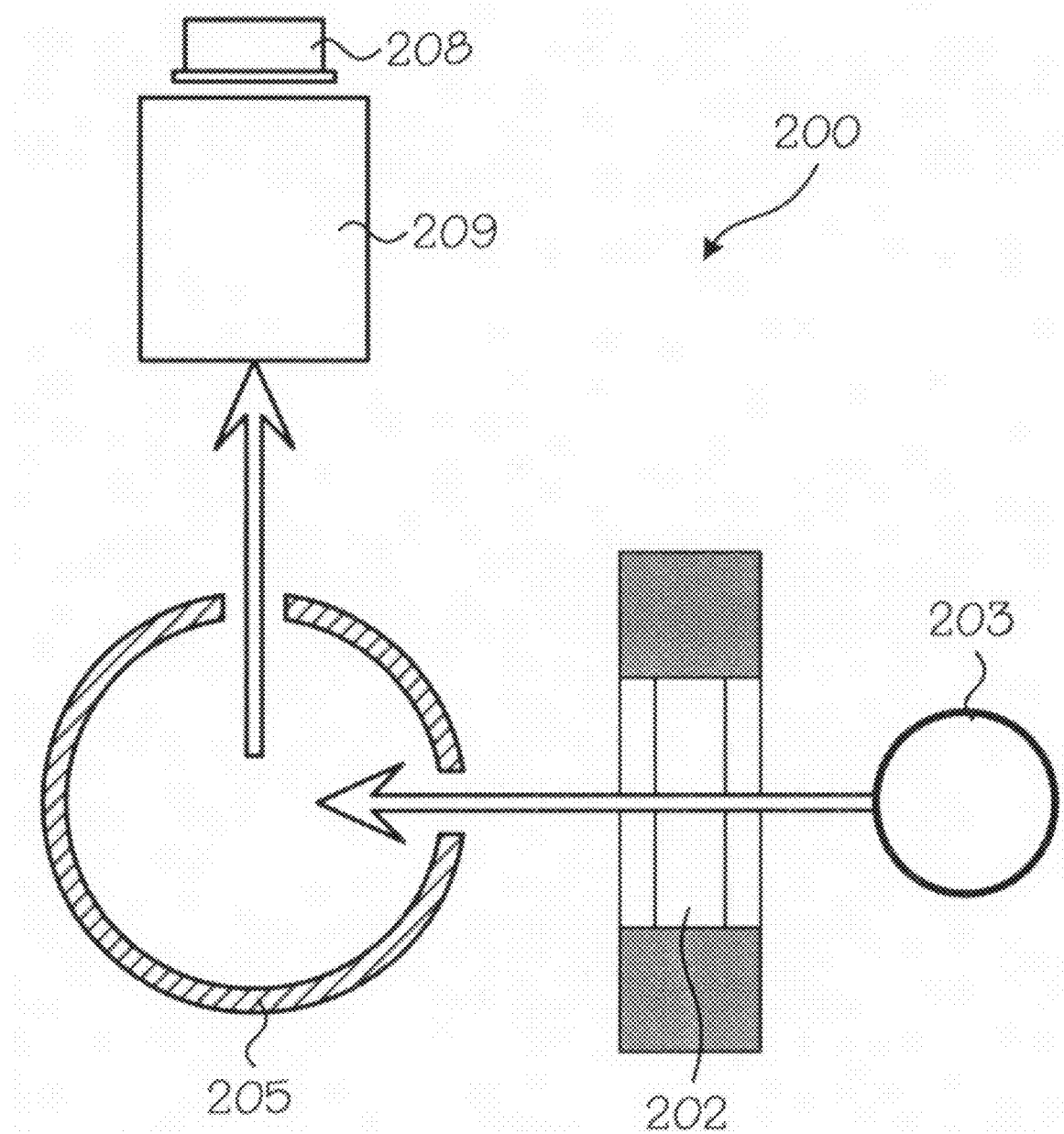
FIG. 2 is a diagram of the measurement device used to assess the relative transmission $1_T$ of windows with varying amounts of coating film and clouding in accordance with an exemplary embodiment of the present invention.

FIG. 2 is a diagram of the measurement device used to assess the relative transmission $l_T$ of windows with varying amounts of coating film and clouding in accordance with an exemplary embodiment of the present invention. The device is generally comprised of radiation source (light source) 203, for generating light having a broad spectral range, or alternatively radiation source 203 may be comprised of a plurality of light sources that may be substituted for one another for emitting light in various regions of the spectrum. The light source selected for one test was a continuous infrared lamp which is typically used in a laboratory to heat items. This particular lamp has an infrared transmission filter and produced a nearly continuous blackbody spectrum. Test window 202 is disposed directly between light source 203 and a port on integration sphere 205. The radiation from light source 203 passed through test window 202 and entered a port of integration sphere 205 (a standard integrating sphere available from the LOT-Oriel Nordic Division in Stockholm, Sweden was used). Integrating sphere 205 creates a uniform distribution of the radiation to fill entrance slit of spectrograph 209. The spectrograph is located at another port of integrating sphere 205 at a right angle to the input port. The transmission measurements were made using a SD512NIR spectrometer available form Verity Instrument, Inc., of Carrollton, Tex., USA. Spectrograph 209 utilizes sensor 208 for converting the spectral light into a signal.

Here it should be mentioned, that the sensor selected for evaluating the relative transmission $l_T$ of window 202 (and the coating film thereon), should exhibit good quantum efficiencies across the spectral region under investigation, i.e., spectral region under investigation should be within the spectral operating range of the sensor. For the example discussed below, an InGaAs diode array sensor was utilized.

For the purposes of describing the present invention, three test windows with varying amounts of clouding were tested. The three test windows had progressively longer exposure to the plasma chemistry. Window 1 had the shortest exposure and has lightly clouded, pale yellow appearance, i.e., the coating film is slightly visible; window 2 had a longer exposure and has marginally clouded appearance with a darker yellow appearance, i.e., the film is clearly visible with darker appearance than that of window 1, but not opaque; and window 3 had the longest exposure to the plasma chemistry and has a highly clouded, dark brown appearance, i.e., the film is highly visible with a darken appearance and approaches opacity.

Figure 3:
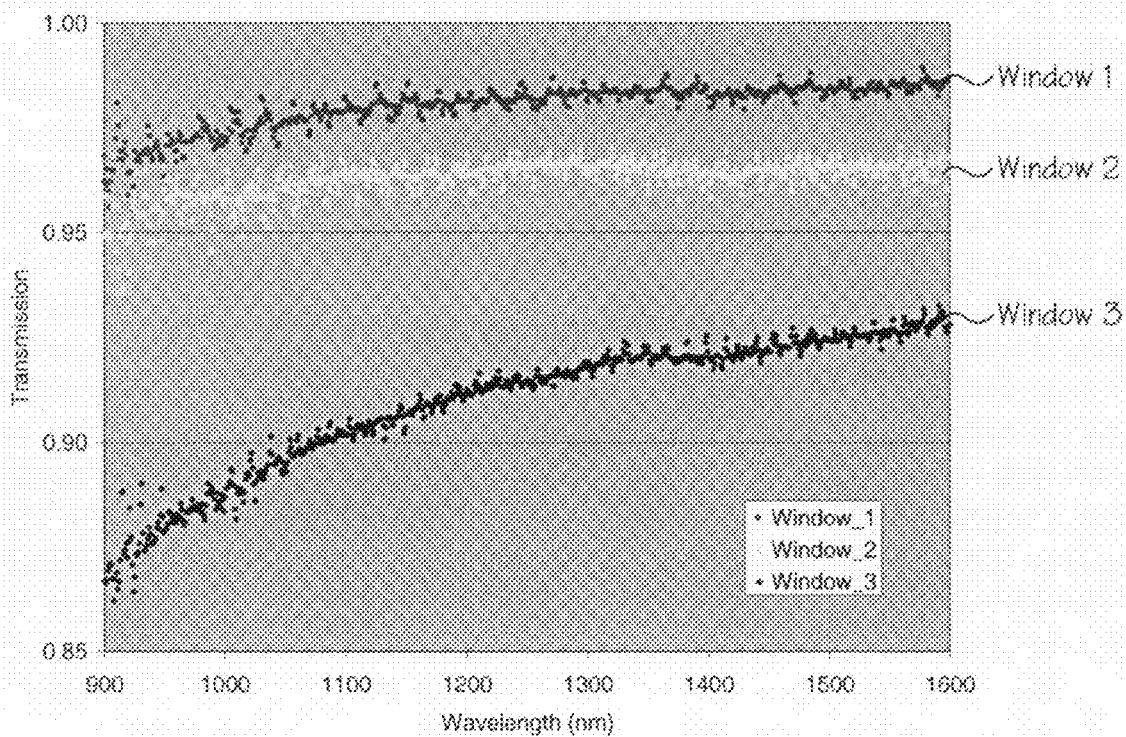
FIG. 3 is a chart showing the transmission response across the near infrared spectral region for three windows with varying amounts of coating film in accordance with an exemplary embodiment of the present invention.

FIG. 3 is a chart depicting the results of that investigation. The chart in FIG. 3 shows the transmission response across the near infrared spectral region for three windows with varying amounts of coating film in accordance with an exemplary embodiment of the present invention. In obtaining the measurements, care was taken that the radiation passed through the darkest portion of the film on the window. Notice that the relative transmission $1_T$ for window 1 is fairly linear and is extremely high, generally above relatively 0.97. The results for window 2 are similar, although slightly lower relative transmission $1_T$ approximately linear and above 0.96 between 1100 nm and 1600 nm. Even window 3, which had an almost opaque coating in visible light, exhibited a marked improvement in the NIR region. Notice in the chart in FIG. 3 that for window 3, with the highly clouded, dark brown appearance, the relative transmission $1_T$ is over 0.85 (that is 85% of all NIR radiation is transmitted across the coating film) and approximately linear in the longer wavelengths of the NIR region.

From the transmission chart, it can be seen that the transmission of the windows corresponds to their appearance and the length of exposure to the plasma. The decrease in transmission includes absorption by the film on the window and reflection losses at the interfaces. The films absorb most of the visible light. However, they are nearly transparent in the NIR, to varying degrees, but depending on their length of exposure to the plasma.

Figure 4:
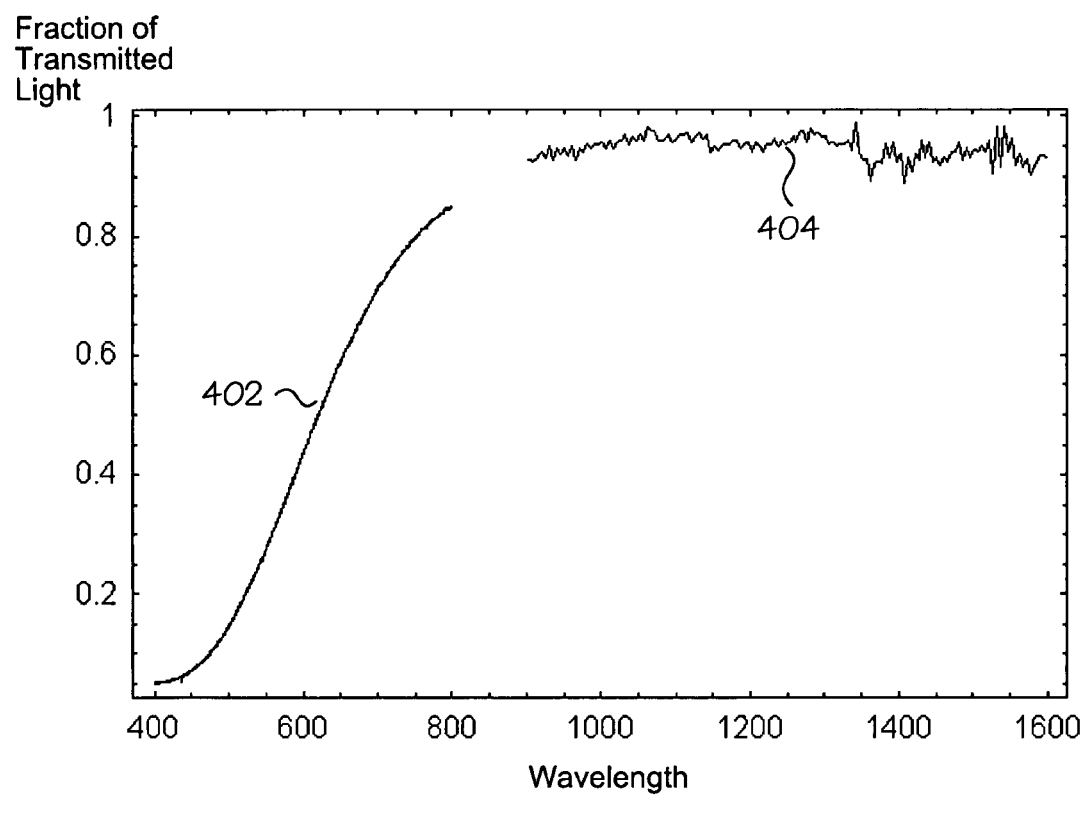
FIG. 4 is a chart showing the transmission response across the UV, visible and near infrared spectral regions for the highly clouded window 1.

FIG. 4 is a chart showing the transmission response across the UV, visible and near infrared spectral regions for the highly clouded window 1. Measured transmission curve 402 shows the relative transmission for window 3 in the UV and visible regions of the radiation spectrum that is typically used for measurements in the semiconductor industry, by using, for example, a Si-type CCD sensors. An appropriate light source was used in the measurements for producing UV-visible light. Notice that the relative transmission is very low at the higher frequencies and, therefore, the absorption to the UV-visible wavelengths is extremely large. Furthermore, measured transmission curve 402 demonstrates that the response across the UV-visible regions is highly wavelength-dependent and correspondingly less desirable for obtaining optical measurements. Measured transmission curve 404, on the other hand, shows the relative transmission across the NIR region of the radiation spectrum (approximately 900 nm-1700 nm). As mentioned above, these measurements were obtained using an InGaAs diode array sensor. Notice here that the response in the NIR region is much more transmissive, i.e., the coating film absorbs less light in the NIR region. Also notice that, as seen in FIG. 3 above, measured transmission curve 404 is approximately independent of wavelength and the relative transmission $1_T$ is over 0.85 across the entire NIR region.

It should be mentioned that an acceptable value for the relative transmission $1_T$ of a window depends on the particular application that the measurement is applied. For example, certain applications, such as diagnostic measurements, are less tolerant to light absorption and consequently the relative transmission threshold will be higher for them, perhaps on the order of ≈0.99. Other applications, for example endpoint measurements may be more tolerant of absorption, for instance with relative transmission threshold of >0.85.

The intent is to identify a spectral region that have low absorption in the coating film and is useful in a particular determination. Merely identifying a region with a high relative transmission for obtaining optimal measurements is not necessarily meaningful unless the optical measurements from that region are compatible with the particular algorithm that is being used. It is possible to identify spectral regions with exceptional transmission, but determinations from these data leads to inconclusive or invalid results. Hence, these regions are of no significance to the particular algorithm being utilized. For instance, in performing endpoint determination optical measurements obtained from a spectral region may have high transmission, but do not exhibit any character that can be associated with the endpoint of a particular process. Consequently, although the optical measurements are relatively unaffected by window clouding, they would not be useful in detecting a process endpoint.

Figure 5:
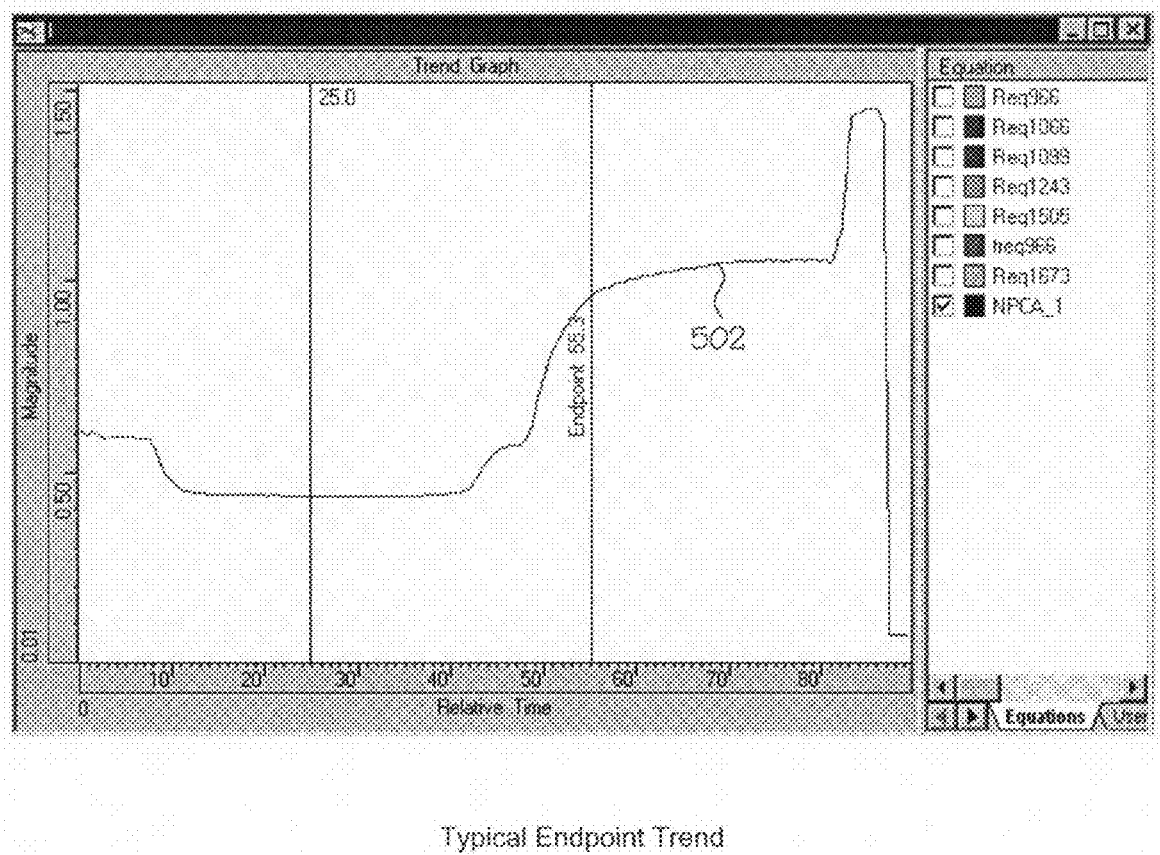
FIG. 5 is a chart depicting a typical endpoint trend for the etch.

Returning to the discussion of the test windows, merely identifying a region with a high relative transmission $1_T$ does not necessarily make the region useful for a particular determination; some character in the measurement should be identified as useful for the determination. To verify this approach, a typical etch was measured in the NIR region. The etch chemistry had $CF_4$, $CHF_3$, Ar, and $O_2$ in a plasma. Layers of ARC and silicon nitride (SiN) were etched in the process. The material that was etched had a photoresist mask and a tungsten silicide stop layer. FIG. 5 shows a typical endpoint trend for the etch. There, intensity curve 502 is the magnitude of the intensity in the NIR region tracked over time during a process. The light with wavelengths from 1000-1550 nm was measured. Notice that the endpoint can be determined as time 55.3 for this process, which validates the NIR region with high transmission as being useful to the particular endpoint determination being utilized.

Figure 6:
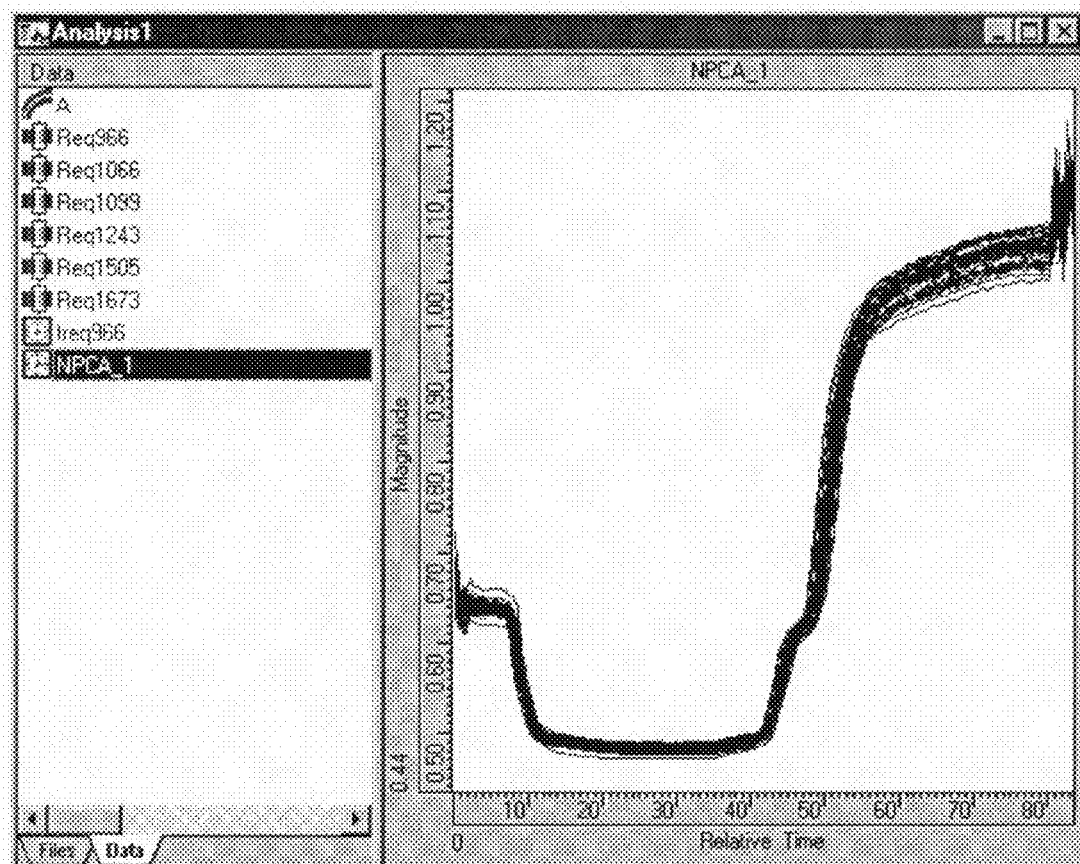
FIG. 6 is a diagram depicting endpoint trends for an etch process that is repeated over an extended time period.

Good transmission in the NIR region also means that extended measurements can be made in a production environment. FIG. 6 is a diagram depicting endpoint trends for an etch process that is repeated over an extended time period. The process was run continuously over a fourteen day period. During that time, 47 measurements were made of the process endpoint. The trends are shown in FIG. 6. These measurements show good reproducibility. The endpoints could be reliably determined, even though the transmission in the visible spectral region had become very poor at the end of the fourteen day period.

Figure 7:
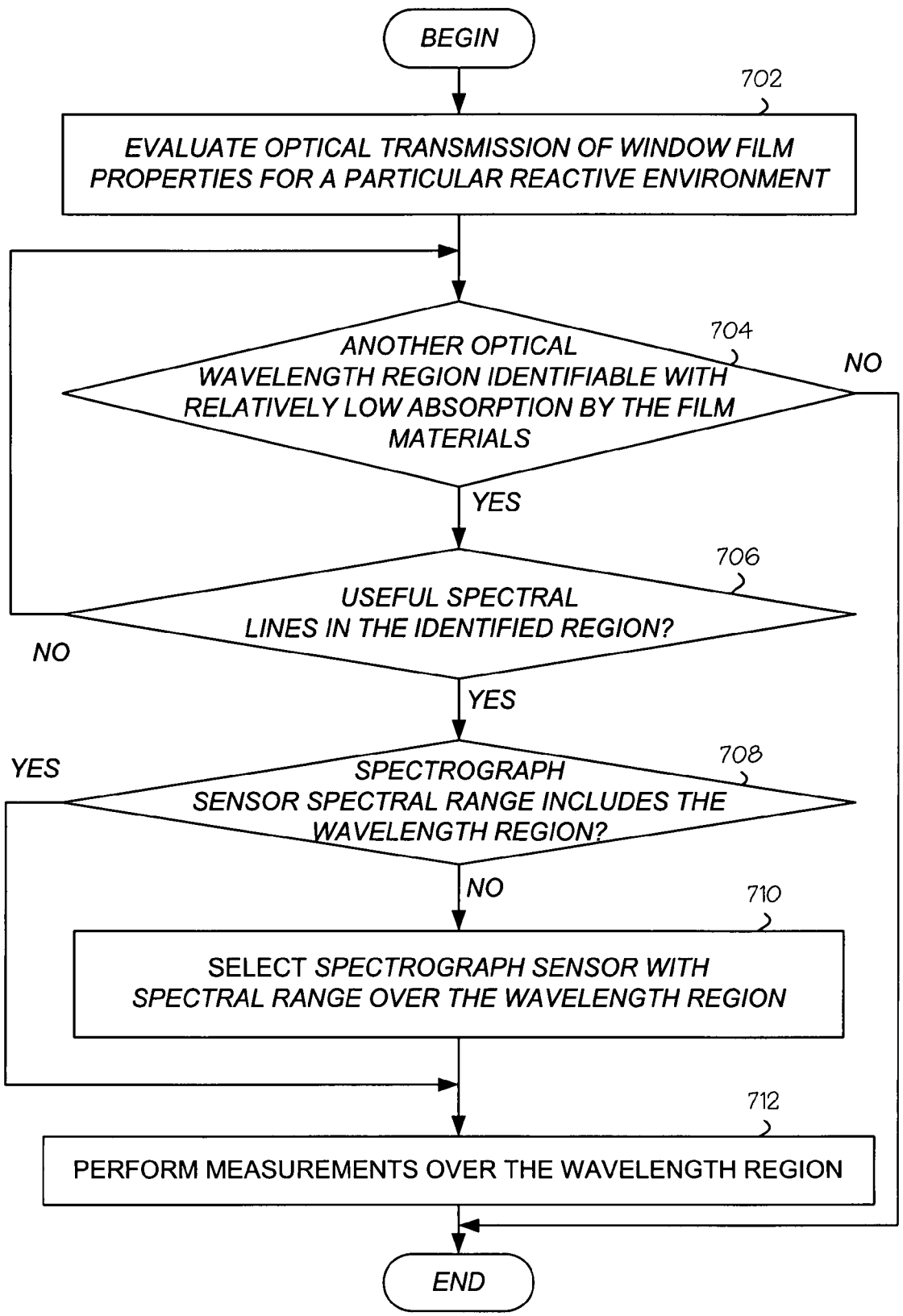
FIG. 7 is a flowchart depicting a method for identifying a spectral region with low absorption that is useful for measurement determinations in accordance with an exemplary embodiment of the present invention.
Figure 8:
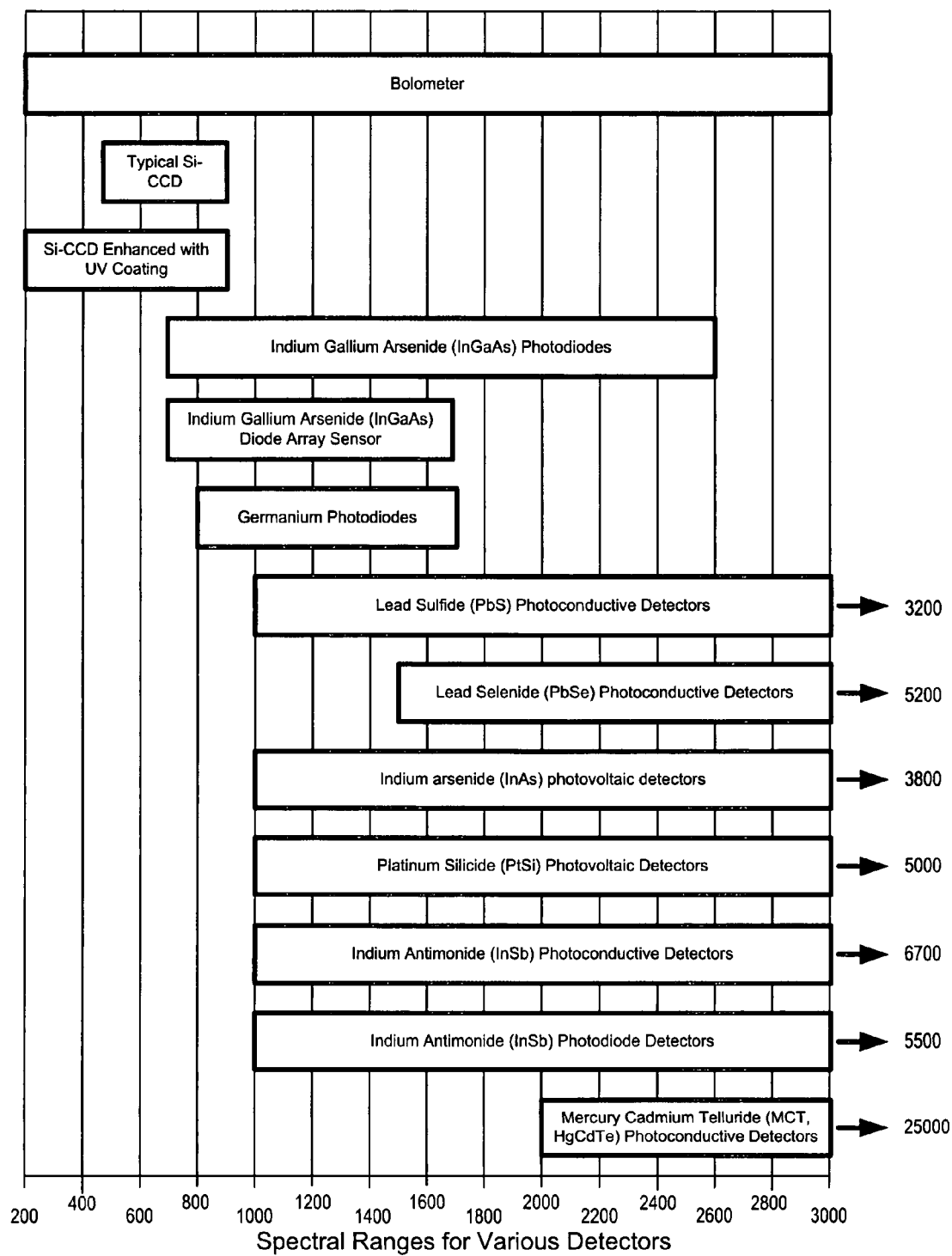
FIG. 8 is a chart showing typical sensor types and their corresponding spectral ranges.

FIG. 7 is a flowchart depicting a method for identifying a spectral region with low absorption that is useful for measurement determinations in accordance with an exemplary embodiment of the present invention. This method is application specific and therefore the results from one application can not necessarily be relied on for another type of reactive environment. Initially, several clouded viewport windows with film coatings should be secured from the reactive environment that the invention is to be used. The relative transmission $1_T$ of these windows will be measured, essentially as discussed above with regard to FIGS. 2 and 3. Test measurement apparatus 200 may be used for this purpose, but it should be understood that light source 203 and sensor 208 should be selected for the wavelength regions under investigation. Therefore, one or more types of sensors may be necessary for obtaining the measurements, depending on the range of the spectral region to be investigated and the spectral range of the sensor (FIG. 8 is a chart showing typical sensor types and their corresponding spectral ranges). Alternatively, a bolometer may be used for obtaining measurement across a wide spectral range rather than several sensors with more narrow spectral ranges. Optimally, a scanning spectrometer may be used for spectrograph 209.

The optical transmission of window film is then measured from the test windows from the particular reactive environment under investigation (step 702). The measurement results are analyzed for a spectral region with relatively low absorption by the film materials (step 704). More than one region may ultimately be identified as having an acceptable relative transmission. Obviously, if no other spectral regions satisfy the relative transmission threshold, the process ends. Once a region of low absorption is detected, that region should be thoroughly checked for usefulness with the particular determination, i.e., the optical measurements exhibit some character that can be used for making a particular determination (step 706). The useful character of a particular region may be apparent to operators familiar with the particular environment or it may be necessary to validate the information obtained from a region in a production environment. If the region is not useful, the process reverts to step 704 and another region with relatively low absorption is identified and then verified as being useful.

Once one or more regions are identified that exhibit good relative transmission to a particular coating film and are useful in a determination, the region can be used in the processing environment, such as with OES measurement apparatus 100 depicted in FIG. 1. Of course, the spectral range of sensor 108 should include the entire range of region identified as having a high relative transmission to the coating film (step 708). If not, sensor 108 of OES measurement apparatus 100 should be replaced with a sensor having an appropriate spectral range (step 710). In either case, optical measurements can proceed on OES measurement apparatus 100 in the identified region. The process then ends.

Using the present invention, especially with regard to the NIR region, allows measurements to be made in a production environment for an extended time period over that known in the prior art and without suffering the adverse effects of window clouding. As should be apparent from the preceding, the aim of the present invention is to identify spectral regions that can both be evaluated using algorithms used in the reactive production process and exhibits a high relative transmission of the coating films typically associated with the reactive production process. It should be expected that during operation, that the window will continue to become clouded. It should also be recognized that the tolerance to light absorption varies with the particular application. As mentioned above, some applications can tolerate a relative transmission value of 0.85, while others are less tolerant. Therefore, it is sometimes advantageous to include a mechanism for decreasing the frequency of window maintenance, e.g., a protective grid, a gas purged viewport, window heater or the like, to further reduce window clouding and extend the time period between maintenance. One particularly good option for extending the time between maintenance is a multichannel array that uses process gas to create the back pressure as disclosed in U.S. patent application Ser. No. 11/726,958.

The exemplary embodiments described below were selected and described in order to best explain the principles of the invention and the practical application, and to enable others of ordinary skill in the art to understand the invention for various embodiments with various modifications as are suited to the particular use contemplated. The particular embodiments described below are in no way intended to limit the scope of the present invention as it may be practiced in a variety of variations and environments without departing from the scope and intent of the invention. Thus, the present invention is not intended to be limited to the embodiment shown, but is to be accorded the widest scope consistent with the principles and features described herein.

The exemplary embodiments were described with regard to an exemplary spectroscopic technique of optical emission spectroscopy. However, the present invention is also useful and applies to other measurement techniques, for example reflectometry, fault detection and characterization (FDC), process monitoring, etc. that requires stable, transparent optical windows that do not degrade or change with time. Although RIE is discussed, it is merely an exemplary environment for practicing the invention, others include, but are not limited to all forms of wet or dry etch, chemical vapor deposition (CVD), chemical-mechanical polishing (CMP), etc. Additionally, the exemplary plasma chemistry used in describing the present invention comprises $CF_4$, $CHF_3$, Ar, and $O_2$. These are not intended to limit or define the invention but merely used as a means to describe certain aspects of the invention. The present invention is applicable to any chemistries and substances that cover, cloud, or contaminate the viewport window. These may relate to monitoring a reaction chamber as discussed, effluent gas monitoring, or other monitoring other emission types.

Furthermore, although Applicant has discovered that the NIR region is particularly useful in some applications, especially in applications where window clouding is prevalent in the UV-visible region, any spectral region may be utilized to reduce the effects of window clouding on a production process. Any spectral region that is identified as having good transmission to the window film can be utilized (assuming that the region contains useful spectral intensity from the plasma).

In describing the present invention, the clouding of a window was described as essentially a polymer film, however the present invention is also useful with window clouding resulting from any material or process that greatly reduces transmission of the window in one region of the spectrum, but reduces transmission much less in another region of the spectrum for the window. Also, although an InGaAs diode array sensor was used for the testing stages, the present invention applies and may utilize other sensor types, including photodiodes, photomultipliers, bolometers, CMOS, charge-coupled devices (CCDs), etc. Consequently, other detector materials may be used including Si, GaAs, HgCdTe, etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

What is claimed is:

1. A method for reducing the effects of window clouding on a viewport window in a reactive environment, comprising:

evaluating an optical transmission of at least one viewport window, said at least one viewport window having reduced transmission from use in a reactive environments comprising:

measuring a first intensity in a path from a radiation source:

measuring a second intensity in the path from the radiation source and through the at least one viewport window; and finding a relative transmission as a ratio of the second intensity to the first intensity;

identifying a spectral region with predetermined optical transmission level, wherein the predetermined optical transmission level is a relative transmission greater than 0.85;

verifying the identified spectral region as compatible with a production algorithm;

monitoring emissions associated with a production process at the identified spectral region; and evaluating the production process by applying the production algorithm to data derived from the identified spectral region.

2. The method in claim 1 further comprises:
obtaining the at least one viewport window used in the reactive environment of the production process, said at least one viewport window having reduced transmission from use in the reactive environment.

3. The method in claim 1, wherein the predetermined optical transmission level is determined by the production algorithm.

4. The method in claim 1, wherein the identified spectral region is the near infrared region of the light spectrum.

5. The method in claim 4, wherein the near infrared region of the light spectrum is between 900 nm and 1700 nm.

6. The method in claim 1, wherein verifying the identified spectral region as compatible with a production algorithm further comprises:
identifying changes in data obtained from the identified spectral region during a production process; and
correlating the changes in data obtained to events in the production process by applying the production algorithm to data derived from the identified spectral region.

7. The method in claim 1, wherein monitoring the identified spectral region during a production process further comprises:
receiving at an Indium Gallium Arsenide sensor type of near infrared sensor.

8. The method in claim 1, wherein the identified spectral region is outside a visible light spectrum.

9. The method in claim 1, wherein the identified spectral region is outside a visible ultraviolet light spectrum.

10. The method in claim 1, wherein the identified spectral region is outside a spectral range of an Si-type of COD detector.

11. The method in claim 1, wherein the predetermined optical transmission level is a relative transmission that is greater than a relative transmission for a visible spectral region.

12. The method in claim 1 further comprises:
protecting the viewport window from contaminants during the production process.

13. The method in claim 1, wherein the production process is one of optical emission spectroscopy (OES), reflectometry, fault detection and characterization (FDC) and process monitoring.

14. The device recited in claim 1, wherein the production process further comprises a $C_yF_x$ chemistry.

15. The method in claim 1, wherein a relative transmission of the at least one viewport window is less than 0.85 in one of a visible light spectrum and a visible ultraviolet light spectrum.

16. The method in claim 1, wherein a relative transmission of the at least one viewport window is less than 0.85 in one of a visible light spectrum and a visible ultraviolet light spectrum.

17. A device for reducing the effects of window clouding on a viewport window in a reactive environment, comprising:
a process chamber comprising:
a plurality of walls which at least partially enclose a process volume;
a material within the process volume; and
a viewport window disposed along one of the walls of the process chamber, said viewport window having a relative transmission of less than 0.99 in at least a portion of one of a visible light spectrum and a visible ultraviolet light spectrum, wherein the relative transmission is a ratio of a first intensity in a path from a radiation source and through the viewport window to a second intensity in a path from the radiation source;
a spectrograph, said spectrograph being optically coupled to said viewport window; and
a near infrared sensor, said near infrared sensor being optically coupled to said spectrograph.

18. The device recited in claim 17, wherein the near infrared sensor has a spectral range of between 900 nm and 1700 nm.

19. The device recited in claim 17, wherein the near infrared sensor is an Indium Gallium Arsenide sensor.

20. The device recited in claim 17, wherein the process chamber further comprises one of a multichannel array, a protective viewport window grid, a viewport window gas purge port and a viewport window heater.

21. The device recited in claim 17, wherein the process chamber further comprises a multichannel array, said multichannel array comprising:
a body having an interior surface and an exterior surface for pneumatically isolating a window chamber pressure within the window chamber from the confinement pressure; and
a predetermined quantity of channels, each of said predetermined quantity of channels having an interior end and an exterior end, a cross-sectional shape with a channel diameter and a channel length between the interior and exterior ends, at least one of said channel diameter, said channel length and said predetermined quantity of channels being related to establishing a flow rate across the predetermined quantity of channels with a pressure differential across the predetermined quantity of channels.

22. The device recited in claim 17, wherein the viewport window has a relative transmission in a near infrared region of the light spectrum of at least 0.85.

23. The device recited in claim 17, wherein the process chamber further comprises a $C_yF_x$ chemistry.

24. The method in claim 17, wherein the spectrograph and near infrared sensor provide measurement information for one of optical emission spectroscopy (OES), reflectometry, fault detection and characterization (FDC) and process monitoring.

25. The method in claim 17, wherein said viewport window having a relative transmission of less than 0.85 in at least a portion of one of a visible light spectrum and a visible ultraviolet light spectrum, wherein the relative transmission is a ratio of a first intensity in a path from a radiation source and through the viewport window to a second intensity in a path from the radiation source.

26. A method for reducing the effects of window clouding on a viewport window in a reactive environment, comprising:
evaluating an optical transmission of at least one viewport window, said at least one viewport window having reduced transmission from use in a reactive environment, comprising:
measuring a first intensity in a path from a radiation source;
measuring a second intensity in the path from the radiation source and through the at least one viewport window; and
finding a relative transmission as a ratio of the second intensity to the first intensity;
identifying a spectral region with predetermined optical transmission level;
verifying the identified spectral region as compatible with a production algorithm, wherein the predetermined optical transmission level is determined by the production algorithm;
monitoring emissions associated with a production process at the identified spectral region; and evaluating the production process by applying the production algorithm to data derived from the identified spectral region.

27. The method in claim 26, wherein the production process is one of optical emission spectroscopy (OES), reflectometry, fault detection and characterization (FDC) and process monitoring.

28. The method recited in claim 26, wherein the production process further comprises a $C_yF_x$ chemistry.

29. A method for reducing the effects of window clouding on a viewport window in a reactive environment comprising a process chamber comprising having a plurality of walls which at least partially enclose a process volume, a material within the process volume; and at least one viewport window disposed along one of the walls of the process chamber, said viewport window having a relative transmission of less than 0.99 in at least a portion of one of a visible light spectrum and a visible ultraviolet light spectrum from use in the reactive environment, wherein the relative transmission is a ratio of a first intensity in a path from a radiation source and through the viewport window to a second intensity in a path from the radiation source, a spectrograph, said spectrograph being optically coupled to said viewport window, and a near infrared sensor, said near infrared sensor being optically coupled to said spectrograph, the method comprising:

evaluating an optical transmssion of the at least one viewport window having a relative transmission of less than 0.99 in at least a portion of one of a visible light spectrum and a visible ultraviolet light spectrum;

identifying a spectral region with predetermined optical transmission level;

verifying the identified spectral region as compatible with a production algorithm;

monitoring emissions associated with a production process at the identified spectral region using the near infrared sensor optically coupled to the spectrograph; and evaluating the production process by applying the production algorithm to data derived from the identified spectral region.

30. The method in claim 29, wherein the production process is one of optical emission spectroscopy (OES), reflectometry, fault detection and characterization (FDC) and process monitoring.

31. The method recited in claim 29, wherein the production process further comprises a $C_yF_y$ chemistry.

* * * * *